US00PP08208P

United States Patent [19]

VandenBerg

[11] Patent Number: Plant 8,208

[45] Date of Patent: Apr. 20, 1993

[54] CHRYSANTHEMUM PLANT NAMED DARK YELLOW BOALDI

[75] Inventor: Cornelis P. VandenBerg, Salinas, Calif.

[73] Assignee: Yoder Brothers, Inc., Barberton, Ohio

[21] Appl. No.: 719,179

[22] Filed: Jun. 21, 1991

[51] Int. Cl.[5] ..... A01H 5/00

[52] U.S. Cl. ..... Plt./78

[58] Field of Search ..... Plt./76, 78

[56] References Cited

U.S. PATENT DOCUMENTS 4,616,099 10/1986 Sparkes ..... 800/1

OTHER PUBLICATIONS

Gosling, ed. 1979, "The Chrysanthemum Manual–6th edition", The National Chrysanthemum Society, London, Essen Telegraph Press, Ltd., 329–336.

Broertjes et al. 1978, "Application of Mutation Breeding Methods in the Improvement of Vegetatively Propagated Crops", Elsevier Sci. Pub. Co., New York, pp. 163–175.

Broertjes et al. 1980, "A mutant of a Mutant of a Mutant of and Irradiation of Progressive Radiation–Induced Mutants in a Marathon Breeding Programme with *Chrysanthemum morifolium*", Euphytica, 29: 526–530.

Searle et al. 1968, "Chrysanthemums the Year Round", Branford Press, London, pp. 27–29, 320–327.

Chan, 1966, "Chrysanthemum and Rose Mutations Induced by X-Rays", Am. Soc. Hort. Sci. Proc., pp. 613–620.

Broertjes, 1966, "Mutation breeding of Chrysanthemums", Euphytica, 15:156–162.

Dowrick et al, 1966, "The induction of mutations in Chrysanthemum using X-and gamma radiation", Euphytica 15:204–210.

*Primary Examiner*—Howard J. Locker

*Attorney, Agent, or Firm*—Foley & Lardner

[57] ABSTRACT

A Chrysanthemum plant named Dark Yellow Boaldi particularly characterized by its flat capitulum form; decorative capitulum type; yellow ray floret color; diameter across face of capitulum of 102 to 114 mm when fully opened, when grown as a pinched disbudded pot mum; photoperiodic flowering response to short days of 52 to 62 days; plant height with 15 to 16 long days after sticking unrooted cuttings, and with 2 applications of 2500 ppm B-9 SP, ranges from 23 to 25 cm when grown as a pinched pot mum with 4 cuttings in a 15 cm pot; branching pattern is spreading and prolific, each plant having 4 to 6 laterals after pinch; and recommended both for disbudded and spray pot mum programs.

1 Drawing Sheet

The present invention comprises a new and distinct cultivar of chrysanthemum, botanically known as *Dendranthema grandiflora,* and referred to by the cultivar named Dark Yellow Boaldi.

Dark Yellow Boaldi, identified as 4068 (81-D11D23), is a product of a mutation induction program. The new cultivar was discovered and selected by Cornelis P. VandenBerg on Oct. 3, 1989 in a controlled breeding program is Salinas, Calif., as one flowering plant within a flowering block established as rooted cuttings from stock plants which had been exposed as unrooted cuttings to an X-ray source of 1500 rads in Fort Myers, Fla., on Apr. 27, 1989. The irradiated parent cultivar was the cultivar identified as Yellow Boaldi, disclosed in plant patent application Ser. No. 07/409,636, now U.S. Plant Pat. No. 7,577 and described as a pot mum with a flat capitulum form, decorative capitulum type, yellow ray floret color, diameter across face of capitulum of 102 to 114 mm when fully opened when grown as a pinched disbudded pot mum, flowering response period of 53 to 66 days after start of short days, plant height of 23 to 30 cm with two applications of 2500 ppm B-9 SP when grown as a pinched pot mum in a 15 cm pot, and a spreading and prolific branching pattern, with 4 to 6 laterals after pinch.

The irradiation program resulting in Dark Yellow Boaldi had as its primary objective to obtain a darker yellow spot of Yellow Boaldi. Earlier irradiation of the grandparent cultivar Boaldi (U.S. Plant Pat. No. 6,613) resulted in the cultivars Cream Boaldi, disclosed in plant patent application Ser. No. 07/409,638, now U.S.

Plant Pat. No. 7,578 and the parent Yellow Boaldi, both of which were later commercially introduced. The ray floret color of both of these is not as deep a yellow as desired by the horitcultural trade, and both Cream Boaldi and Yellow Boaldi were irradiated in an effort to obtain a deeper yellow ray floret color.

The irradiation program comprised irradiating cuttings of Cream Boaldi at irradiation levels of 1500, 1750 and 2000 rads. A total of 934 cuttings harvested from a total of 225 irradiated plants were planted on Jul. 31, Jul. 24 and Jul. 10, 1989. Of these, 4 initial selections were made, which selections were then revegetated and reflowered. Four consecutive flowerings resulted in discarding all 4 initial selections on Jul. 9, 1990. Cuttings of Yellow Boaldi were also irradiated at irradiation levels of 1500, 1750 and 2000 rads. A total of 1043 cuttings harvested from a total of 225 irradiated plants were planted on Jul. 31, Jul. 24 and Jul. 10, 1989. Of these, 18 initial selections were made, which selections were then revegetated and reflowered. Four consecutive flowerings of these 18 selections resulted in discarding 17 selections on Jul. 9, 1990, with only one selection remaining. The ray floret color of this remaining selection was sufficiently darker than the ray floret color of the parent Yellow Boaldi to warrent introduction as Dark Yellow Boaldi.

The first act of asexual reproduction of Dark Yellow Boaldi was accomplished when vegetative cuttings were taken from the initial selection in December 1989 in a controlled environment in Salinas, Calif., by technicians working under supervision of Cornelis P. VandenBerg.

Horticultural examination of controlled flowerings of successive plantings has shown that the unique combination of characteristics as herein disclosed for Dark Yellow Boaldi are firmly fixed and are retained through successive generations of asexual reproduction.

Dark Yellow Boaldi has not been observed under all possible environmental conditions. The phenotype may vary significantly with variations in environment such as temperature, light intensity and daylength.

The following observations, measurements and comparisons describe plants grown in Salinas, Calif., under greenhouse conditions which approximate those generally used in commercial greenhouse practice.

The following traits have been repeatedly observed and are determined to be basic characteristics of Dark Yellow Boaldi, which, in combination, distinguish this Chrysanthemum as a new and distinct cultivar:

1. Flat capitulum form.
2. Decorative capitulum type.
3. Yellow ray floret color.
4. Diameter across face of capitulum of 102 to 114 mm when fully opened, when grown as a pinched disbudded pot mum.
5. Photoperiodic flowering response to short days of 52 to 62 days.
6. Plant height, with 15 to 16 long days after sticking unrooted cuttings, and with 2 applications of 2500 ppm B-9 SP, ranges from 23 to 25 cm when grown as a pinched pot mum with 4 cuttings in a 15 cm pot.
7. Branching pattern is spreading and prolific, each plant having 4 to 6 laterals after pinch.
8. Recommended for both disbudded and spray pot mum programs.

The accompanying photographic drawing is a top perspective view of potted plants of Dark Yellow Boaldi, with 4 cuttings in a 15 cm pot, with the colors being as nearly true as possible with illustration of this type.

Of the commercial cultivars known to the inventor, the most similar in comparison to Dark Yellow Boaldi is the parent cultivar Yellow Boaldi. All traits of Dark Yellow Boaldi are similar to those of Yellow Boaldi, except for the ray floret color. When comparing the description of Dark Yellow Boaldi with Yellow Boaldi, it is evident that Yellow Boaldi has a wider range of flowering response and plant height than Dark Yellow Boaldi. The reason for this is that the description of Yellow Boaldi is based on evaluations over a 2 year time period, while the description of Dark Yellow Boaldi is based on 7 flowerings in a 9 month period.

In the following description color references are made to The Royal Horticultural Society Colour Chart. The color values were taken from plant material grown as a pinched disbudded pot mum in Salinas, Calif. on Apr. 1, 1991.

Classification:

*Botanical.*—*Dendranthema grandiflora* cv Dark Yellow Boaldi.

*Commercial.*—Flat decorative disbud and spray pot mum.

INFLORESCENCE

A. Capitulum:

*Form.*—Flat.

*Type.*—Decorative.

*Diameter across face.*—102 to 114 mm when fully opened when grown as a pinched disbudded pot mum.

B. Corolla of ray florets:

*Color (general tonality from a distance of three meters).*—Yellow.

*Color (upper surface).*—3B to 3C, with center of flower closest to 3A. This color is significantly darker than the ray floret color of Yellow Boaldi (4B to 4C), and much darker than the pale yellow ray floret color (2D to 4D) of Cream Boaldi.

*Color (under surface).*—3B to 3C.

*Shape.*—Flat, oblong.

C. Corolla of disc florets:

*Color (mature).*—Closest to 154B.

*Color (immature).*—Closest to 144B.

D. Reproductive organs:

*Androecium.*—Present on disc florets only; scant pollen.

*Gynoecium.*—Present on both ray and disc florets.

PLANT

A. General appearance:

*Height.*—23 to 25 cm when grown as a pinched pot mum with 15 to 16 long days prior to start of short days and with 2 applications of 2500 ppm B-9 SP.

*Branching pattern.*—Spreading and prolific, with 4 to 6 laterals after pinch.

B. Foliage

*Color (upper surface).*147A.

*Color (under surface).*147B.

*Shape.*—Lobed and serrated.

I claim:

1. A new and distinct Chrysanthemum plant named Dark Yellow Boaldi, as described and illustrated.

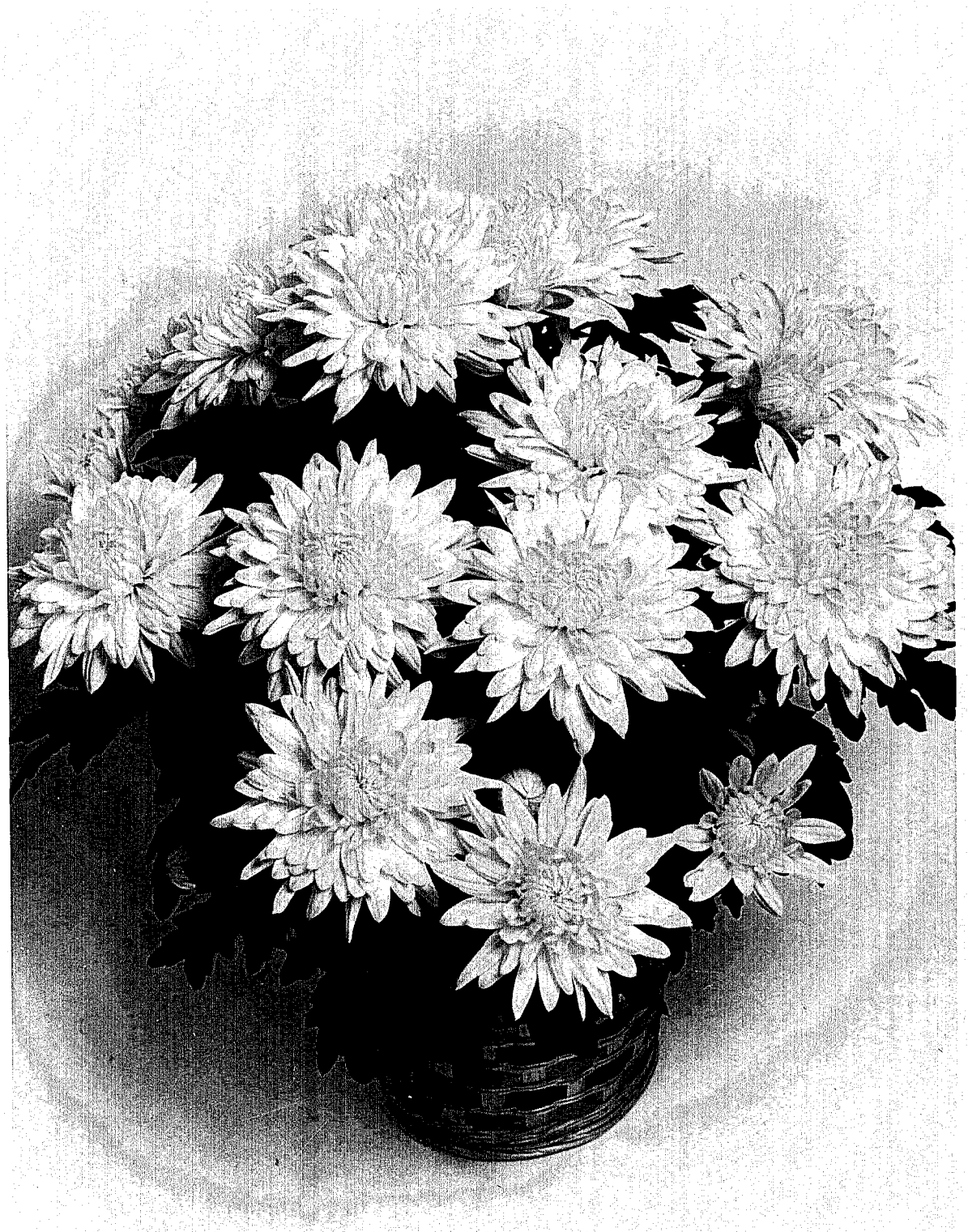

* * * * *